(12) United States Patent
Guerry et al.

(10) Patent No.: US 7,700,578 B2
(45) Date of Patent: Apr. 20, 2010

(54) **CAPSULE COMPOSITION FOR USE AS IMMUNOGEN AGAINST *CAMPYLOBACTER JEJUNI***

(75) Inventors: Patricia Guerry, Silver Spring, MD (US); Mario Artur Monteiro, Guelph (CA)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/221,150

(22) Filed: Jul. 25, 2008

(65) Prior Publication Data

US 2009/0004223 A1 Jan. 1, 2009

Related U.S. Application Data

(63) Continuation-in-part of application No. 11/524,057, filed on Sep. 20, 2006.

(60) Provisional application No. 60/962,313, filed on Jul. 27, 2007, provisional application No. 60/722,086, filed on Sep. 21, 2005.

(51) Int. Cl.
*C07H 3/00* (2006.01)
*C13K 5/00* (2006.01)
*A61K 31/715* (2006.01)
*A01N 43/04* (2006.01)

(52) U.S. Cl. .................. 514/55; 514/53; 536/123.1; 536/123.13; 424/234.1

(58) Field of Classification Search ................ None
See application file for complete search history.

(56) References Cited

U.S. PATENT DOCUMENTS 5,153,312 A 10/1992 Porro et al.
5,869,066 A 2/1999 Pace et al.

OTHER PUBLICATIONS

Aspinall et al. Eur. J. Biochem 231, 570-578 (1995).*
Papp-Szabo et al. Cell Suface alpha glucan in *C. jejuni* 81-176. Carbohydrate Research vol. 340, 13:2218-2221, Sep. 2005, available online Aug. 1, 2005.
Karlyshev, et al. Analysis of *C. jejuni* Capsular Loci reveals Multiple mechanisms for generation of structural diversity. Mol. Micro. Jan. 2005 vol. 55 p. 90-103.
Aspinall et al. Structure of O chains from Lipopolysaccharides of *C. jejuni* Serotypes O:23 and O:26. Carbohydrate Research 231:13-30, 1992.
Kanipes et al., Mutation of waaC encoding heptotransferase in *C. jejuni* 81-176 affecting the structure of both LPS and CPS.The Journal of Bacteriology, May 2006. p. 3273-3279.
Guerry et al., Phase variation of *C.jejuni* 81-197 LPS affecting gangolioside mimicry & invasiveness in vitro. Infection and Immunity, Feb. 2002, p. 787-793.
Ritter et al. Induction of antibodies reactive with GM2 ganglioside after immunization with Lipopolysaccharides from *Campylobacter jejuni*. Int. J. Cancer 66:190-194, 1996.
Aspinall et al. Diversity of Lipopolysaccharide Structures in *Campylobacter jejuni*. The Journal of Infectious Disease 1997; 176:s135-8.
Bagar et al. Safety & Immunogenecity of a prototype Oral WholeCell killed *Campylobacter* vaccine adminstered w/ a Mucosal Adjuvant in Non-human Primates Vaccine. 1995, v13.

* cited by examiner

*Primary Examiner*—Robert Mondesi
*Assistant Examiner*—Oluwatosin Ogunbiyi
(74) *Attorney, Agent, or Firm*—Joseph K. Hemby, Jr.; Albert M. Churilla; Ning Yang (57) ABSTRACT

An immunogenic composition, and method of using the composition to elicit an immune response to *Campylobacter jejuni*. The composition is an isolated polysaccharide polymer composed of one or more forms of disaccharide polymers.

26 Claims, 8 Drawing Sheets

CAPSULE COMPOSITION FOR USE AS IMMUNOGEN AGAINST *CAMPYLOBACTER JEJUNI*

CROSS-REFERENCE TO RELATED APPLICATIONS

This application claims the benefit of Provisional Application Ser. No. 60/962,313, filed Jul. 27, 2007, and is a Continuation-in-Part application of U.S. patent application Ser. No. 11/524,057, filed Sep. 20, 2006, which claims benefit of Provisional Application Ser. No. 60/722,086, filed Sep. 21, 2005 and is related to PCT application PCT/US06/36619, filed Sep. 20, 2006, all of which are incorporated by reference.

FIELD OF INVENTION

The inventive subject matter relates to an immunogenic composition capable of conferring protection against diarrhea caused by *Campylobacter jejuni* and a method of inducing an immune response to said composition.

BACKGROUND OF INVENTION

*C. jejuni* is a leading cause of diarrheal disease worldwide and a documented threat to US military personnel (Taylor, 1992; Tauxe, 1992). The symptoms of *campylobacter* enteritis include diarrhea, abdominal pain, and fever and often accompanied by vomiting. Stools usually contain mucus, fecal leukocytes, and blood, although watery diarrhea is also observed (Cover and Blaser 1999). However, despite the importance of this organism to human disease, there are no licensed vaccines against *C. jejuni.*

Because of the medical importance of *C. jejuni*, considerable research is dedicated toward understanding the pathogen. However, notwithstanding this effort, there is surprisingly little understanding about how *C. jejuni* causes human disease. The genome of one strain, NCTC 11168 (Parkhill, et al., 2000) revealed several unusual aspects about the biology of *C. jejuni*. One striking feature is the presence of an unexpectedly high number of genes encoding putative enzymes involved in sugar and/or polysaccharide synthesis (Parkhill et al., 2000). The sequence, and resulting research fostered primarily by the availability of the sequence, has revealed that these genes fall into 4 main functional clusters that underscore the importance of some unusual carbohydrate structure to the biology of *C. jejuni*. These clusters include Lipooligosaccharide (LOS) synthesis, genetic control of flagellin glycosylation, genetic control of N-linked glycosylation, and the control of the biosynthesis and assembly of capsule.

Vaccine strategies against *C. jejuni* have been largely limited due to the molecular mimicry between lipooligosaccharide (LOS) cores of many strains of *C. jejuni* and human gangliosides (Moran, et al., 1996). This mimicry is thought to be a major factor in the strong association of *C. jejuni* infection with Guillain Barre Syndrome (GBS), a post-infectious polyneuropathy (Allos, 1997). Thus, antibodies generated against LOS cores result in an autoimmune response to human neural tissue. It has been estimated that as many as 1/3000 cases of *campylobacter* enteritis results in GBS. Therefore, the possibility of developing GBS could be associated with any whole cell vaccine against *C. jejuni* that includes ganglioside mimicry.

LOS synthesis in *Campylobacter* is controlled by a number of genes, including genes encoding enzymes involved in biosynthesis of sialic acid for incorporation into LOS. Thus, *C. jejuni* is one of a limited number of bacteria that can endogenously synthesize sialic acid, a 9 carbon sugar that is found in many mammalian cells. This is consistent with the observed molecular mimicry of LOS and human gangliosides important in GBS (Aspinall et al., 1993, 1994 (a and b); Salloway et al., 1996).

Although glycosylation of proteins was once considered to be a eukaryotic trait, there is an increase awareness of prokaryotic protein glycosylation (Power and Jennings, 2003). The best characterized and most extensively glycosylated bacterial protein is *campylobacter* flagellin. Flagellin from strain 81-176 is glycosylated at 19 serine or threonine sites by an O-linkage to pseudaminic acid and derivatives of pseudaminic acid (Thibault et al., 2001). Pseudaminic acid is an unusual 9 carbon sugar that resembles sialic acid, but which is highly immunogenic, unlike sialic acid. Moreover, mutants that are unable to glycosylate flagellin cannot assemble a flagellar filament (Goon et al, 2003). Since flagella are indispensable virulence determinants of *C. jejuni*, glycosylation is therefore also a key virulence determinant.

One of the most unusual aspects of *C. jejuni* is the presence of a general system for N-linked glycosylation of numerous proteins (Szymanski et al., 1999; reviewed in Szymanski et al., 2003). This system, which includes an oligosaccharide transferase similar to that found in the eukaryote *Saccharomyces cerevisiae*, attaches a glycan which has recently been shown to be a heptasaccharide composed of one bacillosamine residue (an unusual deoxy sugar), one D-glucose, and five D-GalNAc residues (Young et al., 2002). The glycosylation appears to occur on numerous periplasmic, and perhaps, surface exposed proteins in *C. jejuni* (Young et al., 2002). The unusual glycan, again, appears to be highly immunogenic and is recognized during human infection (Szymanski et al., 1999, 2003).

An interesting recent revelation regarding the *Campylobacter* genome sequence was the presence of a complete set of capsule transport genes similar to those seen in type II/III capsule loci in the Enterobactericeae (Parkhill et al., 2000; Karlyshev et al., 2000). Subsequent genetic studies in which site-specific mutations were made in several capsule transport genes indicated that the capsule was the serodeterminant of the Penner serotyping scheme (Karlyshev et al., 2000; Bacon et al., 2001). The Penner scheme (or HS for heat stable) is one of two major serotyping schemes of campylobacters and was originally thought to be based on lipopolysaccharide O side chains (Moran and Penner, 1999).

Currently it is believed that all of the structures previously described as O side chains are, in fact, capsules. The chemical structures of the capsule/O side chains of several Penner serotypes have been determined, and these structures include several unusual sugar structures, as summarized in Table 1. The capsule of the genome strain, NCTC 11168, contains a heptopyranose as a L-gluco conformer, which is the first report of such a structure in nature (St. Michael et al., 2002). The capsule of the type strains HS23 and HS36 contain the same carbohydrates in different ratios, and include a mixture of 4 unusual altro-heptoses (6-deoxy-α-D-altro-heptose, D-glycero-α-D-altro-heptose, 6-deoxy-3-Me-α-D-altro-heptose, and 3-Me-D-glycero-α-D-altro-heptose (Aspinall et al., 1992).

TABLE 1

Structure of some capsular polysaccharides of *C. jejuni* strains.

| Strain | Structure | Reference |
|---|---|---|
| HS3 | →4-α-D-Gal-(1→3)(3-hydroxypropanoyl)-L-glycero-α-D-ido-Hep-(1→ | Aspinall et al., 1995 |
| HS19 | →4)-β-D-GlcA-(1→3)-β-D-GlcNAc-(1→<br>(the GlcA units are present as amides of 2-amino-2-deoxyglycerol) | Aspinall et al., 1994 a, b |
| HS23, HS36 | Four closely-related polysaccharides:<br>→3)-β-D-GlcNAc-(1→3)-α-D-Gal-(1→2)-6d-α-D-altro-Hep-(1→;<br>→3)-β-D-GlcNAc-(1→3)-α-D-Gal-(1→2)-6d-3-O-Me-α-D-altro-Hep-(1→;<br>→3)-β-D-GlcNAc-(1→3)-α-D-Gal-(1-48 2)-D-glycero-α-D-altro-Hep-(1→;<br>→3)-β-D-GlcNAc-(1→3)-α-D-Gal-(1→2)-3-O-Me-D-glycero-α-D-altro-Hep-(1→& | Aspinall et al., 1992 |
| 81116 | Two polysaccharides at a ratio of 3A:1B, where<br><br>$\quad\quad\quad$ OAc (30%) $\quad\quad\quad\quad$ OAc (20%)<br>$\quad\quad\quad\quad\quad\downarrow\quad\quad\quad\quad\quad\quad\quad\quad\quad\downarrow$<br>$\quad\quad\quad\quad\quad 3 \quad\quad\quad\quad\quad\quad\quad\quad\quad 6$<br>A = →3)-β-D-Glc-(1→2)-α-D-GlcA-(1→3)-α-D-Man-(1→3)-α-D-Glc-(1→<br><br>B = →3)-β-G-GlcNAc-(1→6)-α-D-Glc-(1→4)-α-D-Gal-(1→<br>$\quad\quad\quad\quad\quad\quad\quad\quad\quad\quad\quad\quad\quad\quad\quad\quad\quad 3$<br>$\quad\quad\quad\quad\quad\quad\quad\quad\quad\quad\quad\quad\quad\quad\quad\quad\quad\uparrow$<br>$\quad\quad\quad\quad\quad\quad\quad\quad\quad\quad\quad$ β-D-GlcNAc-(1 | Muldoon et al. (2002) |
| NCTC 11168 | 6-O-Me-D-L-α-L-glc-Hepp-(1<br>$\quad\quad\quad\quad\quad\quad\quad\quad\quad\quad\quad\quad\quad\downarrow$<br>→2)-β-D-Ribf-(1→5)-β-D-GalfNAc-(1→4)-α-D-GlcpA6(NGro)-(1→<br>(Here, Glucuronic acid is amidated with 2-amino-2-deoxyglycerol at C-6) | St. Michael et al. (2002) |

There are several examples of highly effective capsular vaccines. *S. pneumoniae* has 83 different capsular types, but the current *S. pneumoniae* vaccine contains a mixture of the 23 most prevalent serotypes in the US and Europe. *N. mengiditis* has fewer serogroups, thus potentially simplifying vaccine development, and, in fact, serogroups A, B and C are responsible for >90% of cases of meningococcal meningitis (Jennings, 1990). However, the polysaccharide from serotype B is poorly immunogenic in man, likely because it mimics human tissues. Capsular vaccines have also been developed against *H. influenzae* and Group B *Streptococcus*.

As previously mentioned, there currently are no licensed vaccines against *Campylobacter*, due greatly to the molecular mimicry between LOS cores of many strains of *C. jejuni* and human gangliosides (Moran, et al., 1996). However, vaccine formulations incorporating bacterial capsules have been developed against a number of pathogens. In general, capsule vaccines are immunogenic in humans and non-toxic (Jennings, 1990). One of the general problems associated with capsule vaccines is the poor immunogenicity of all polysaccharides in infants, and the fact that many of the capsular vaccines are directed at diseases that are particular threatening to the pediatric population. Based on murine studies, pure polysaccharide antigens are considered to be T cell independent, and capable of inducing only IgM type responses. Adult humans, in contrast, are able to generate IgG, in addition to IgM and IgA antibodies against polysaccharides. Responses in infants to vaccines against type B *H. influenzae* (Schneerson et al 1980; Anderson, 1983; Marburg, 1986), group A, B and C *Neisseria meningiditis* (Jennings and Lugowski, 1981 and 1983; and type 6A *Streptococcus pneumoniae* (Chu et al., 1983) have all improved following conjugation to proteins.

*C. jejuni* capsule, as defined in this application, is a generic term for capsular polymers, which are composed of repeating polysaccharide structures. The repeating structures can be homopolymers, defined as a repeating single sugar moiety, or repeating oligosaccharides (i.e. disaccharides or trisaccharides, etc.). A number of species of capsular repeating polysaccharide polymers have been identified. To illustrate the genus of capsular polysaccharide structures, Table 2 lists known capsular polysaccharide structures for *Campylobacter* strains.

TABLE 2

| Strain/HS type | Structure | Reference |
|---|---|---|
| HS3 | →4-α-D-Gal-(1→3)(3-hydroxypropanoyl)-L-glyero-α-D-ido-Hep-(1→ | Aspinall, et al (1995 |
| HS19 | →4)-β-D-GlcA-(1→3)-β-D-GlcNAc-(1→<br>(GlcA units are present as amides of 2-amino-2-deoxyglycerol) | Aspinall, et al., 1994 (a and b) |
| HS23/36 | Four closely-related polysaccharides:<br>→3)-β-D-GlcNAc-(1→3)-α-D-Gal-(1→2)-6d-α-D-altro-Hep-(1→;<br>→3)-β-D-GlcNAc-(1→3)-α-D-Gal-(1→2)-6d-α-O-Me-α-D-altro-Hep-(1→;<br>→3)-β-D-GlcNAc-(1→3)-α-D-Gal-(1→2)-D-glycero-α-D-altro-Hep-(1→;<br>→3)-β-D-GlcNAc-(1→3)-α-D-Gal-(1→2)-3-O-Me-D-glycero-α-D-altro-Hep(1→ | Aspinall, et al., 1992 |

TABLE 2-continued

| Strain/HS type | Structure | Reference |
|---|---|---|
| 81116 (HS6) | Two polysaccharides at a ratio of 3A:1B, where:<br><br>$\quad\quad\quad$ OAc (30%) $\quad\quad\quad\quad\quad$ Oac (20%)<br>$\quad\quad\quad\quad\downarrow\quad\quad\quad\quad\quad\quad\quad\quad\downarrow$<br>$\quad\quad\quad\quad 3\quad\quad\quad\quad\quad\quad\quad\quad 6$<br>A = →3)-β-D-Glc-(1→2)-α-D-GlcA-(1→3)-α-D-Man-(1→3)-α-D-Glc-(1→<br>B = →3)-β-D-GlcNAc-(1→6)-α-D-Glc-(1→4)-α-D-Gal-(1→<br>$\quad\quad\quad\quad\quad\quad\quad\quad\quad\quad\quad\quad\quad\quad\quad\quad\quad\quad\quad 3$<br>$\quad\quad\quad\quad\quad\quad\quad\quad\quad\quad\quad\quad\quad\quad\quad\quad\quad\quad\quad\uparrow$<br>$\quad\quad\quad\quad\quad\quad\quad\quad\quad\quad\quad\quad\quad\quad\quad\quad\text{β-D-GlcNAc-(1}$ | Muldoon, et al., 2002 |
| NCTC 11168(HS2) | 6-O-Me-D-L-α-L-glc-Hepp-(1<br>$\quad\quad\quad\quad\quad\quad\quad\quad\quad\quad\quad\downarrow$<br>→2)-β-D-Ribf-(1→5)-β-D-GalfNAc-(1→4)-α-D-GlcpA6(Ngro)-(1→ (Glucuronic acid is amidated with 2-amino-2-deoxyglycerol at C-6) | St. Michael, et al., 2002 |
| HS41 | Two closely related polysaccharides:<br>→2)-β-L-Araf-(1→2)-β-D-6d-altro-Hepf-(1→2)-β-L-6d-altrof-(1→ (75%; and<br>→2)-β-L-Araf-(1→2)-β-D-6d-altro-Hepf-(1→2)-α-D-Fucf-(1→ (25%) | Hannify, et al., 1999 |
| HS30 (C. coli) | $\quad\quad\quad\quad\quad\quad$→5-Ribitol-1-P→<br>$\quad\quad\quad\quad\quad\quad\quad\quad\quad 2$<br>$\quad\quad\quad\quad\quad\quad\quad\quad\quad\uparrow$<br>6d-β-D-talo-Hep-(1→4)-β-D-GlcNAc-(1 | Aspinall, et al., 1993 |
| HS1 | →4)-β-D-Gal-(1→2)-(R)-Gro-(1-P→<br>(with two branches at C-2 and C-3 of Gal of β-D fructofuranoses that are further substituted at C-3 with O-methyl phosphoramidate groups | Aspinall 1998; McNally, et al., 2005 |
| HS4 | →3)-6-d-β-D-ido-Hep-(1→4)-β-D-GlcNAc-(1→<br>With O-methyl phosphoramidate units present in non-stoichiometric amounts at the O-2 and/or O-7 positions of 6-deoxy-beta-D-ido-Heptose. | Chen, et al. 2008 |
| 81-176 (HS23/36) | →3)-α-D-Gal-(1→2)-6d-3-O-Me-α-D-altro-Hep-(1→3)-β-D-GlcNAc-(1→<br>$\quad\quad\quad\quad\quad 2$<br>[MeOP(O)N]$^\pm$ | Kanipes, et al., 2006 |

SUMMARY OF INVENTION

An object of this invention is an anti-C. jejuni immunogenic composition, composed of a capsule polysaccharide polymer, capable of inducing an immune response against important pathogenic strains C. jejuni without concomitantly inducing GBS.

Another object of the invention is an anti-C. jejuni prophylactic formulation with enhanced T-cell dependent immunity to important pathogenic strains of the bacteria by conjugating the capsule of C. jejuni to T-dependent carrier molecules.

Yet, another object of the invention is a method of administering the carrier conjugated or unconjugated anti-C. jejuni capsule polysaccharide composition in order to induce an immune response.

DESCRIPTION OF DRAWINGS

FIG. 2. (A) $^1$H-NMR spectrum of the capsular polysaccharide of C. jejuni strain BH0142 showing that this capsular polysaccharide, and (B) $^{31}$PNMR spectrum of the capsular polysaccharide of C. jejuni strain BHO 142 showing that this capsular polysaccharide contains several O-methyl-phosphoramidate units.

FIG. 5. (A) Scheme showing the conjugation of the activated C. jejuni strain BH0142 capsular polysaccharide to the carrier protein CRM$_{197}$, and (B) Scheme showing the conjugation of the activated C. jejuni strain CPS8486 capsular polysaccharide to the carrier protein CRM$_{197}$. Either a non-reducing end GlcNAc or a non-reducing end 6d-ido-Hep could be oxidized.

DETAILED DESCRIPTION OF PREFERRED EMBODIMENTS

C. jejuni capsular moieties are important in serodetermination. However, despite over 60 Penner serotypes having been identified, most Campylobacter diarrheal disease is caused by C. jejuni from a limited number of serotypes. Because of the importance of capsule structure in serodetermination, it is postulated that they are highly immunogenic structures. Additionally, they are also unlikely to exhibit the unwanted autoimmune induction caused by immuno-mimicry observed by lipooligosaccharides. Therefore, capsules or capsular components would be highly useful in anti-*C. jejuni* vaccines. *C. jejuni* capsule are composed of repeating polysaccharide structures. The repeating structures can be homopolymers, defined as a repeating single sugar moiety, or repeating oligosaccharides such as disaccharides or trisaccharides.

The chemical composition of *C. jejuni* capsules were analyzed by first growing *C. jejuni* and then isolating and purifying the capsule using water-phenol extraction, ultra-centrifugation and gel permeation chromatography. The specific carbohydrate structures were determined by chemical manipulations in combination with gas-liquid chromatography (GLC), and GLC-mass spectrometry, and fast atom bombardment-mass spectrometry (FAB-MS). Anomeric configuration of the sugars was determined by nuclear magnetic resonance (NMR) spectrometry.

Figure 1:
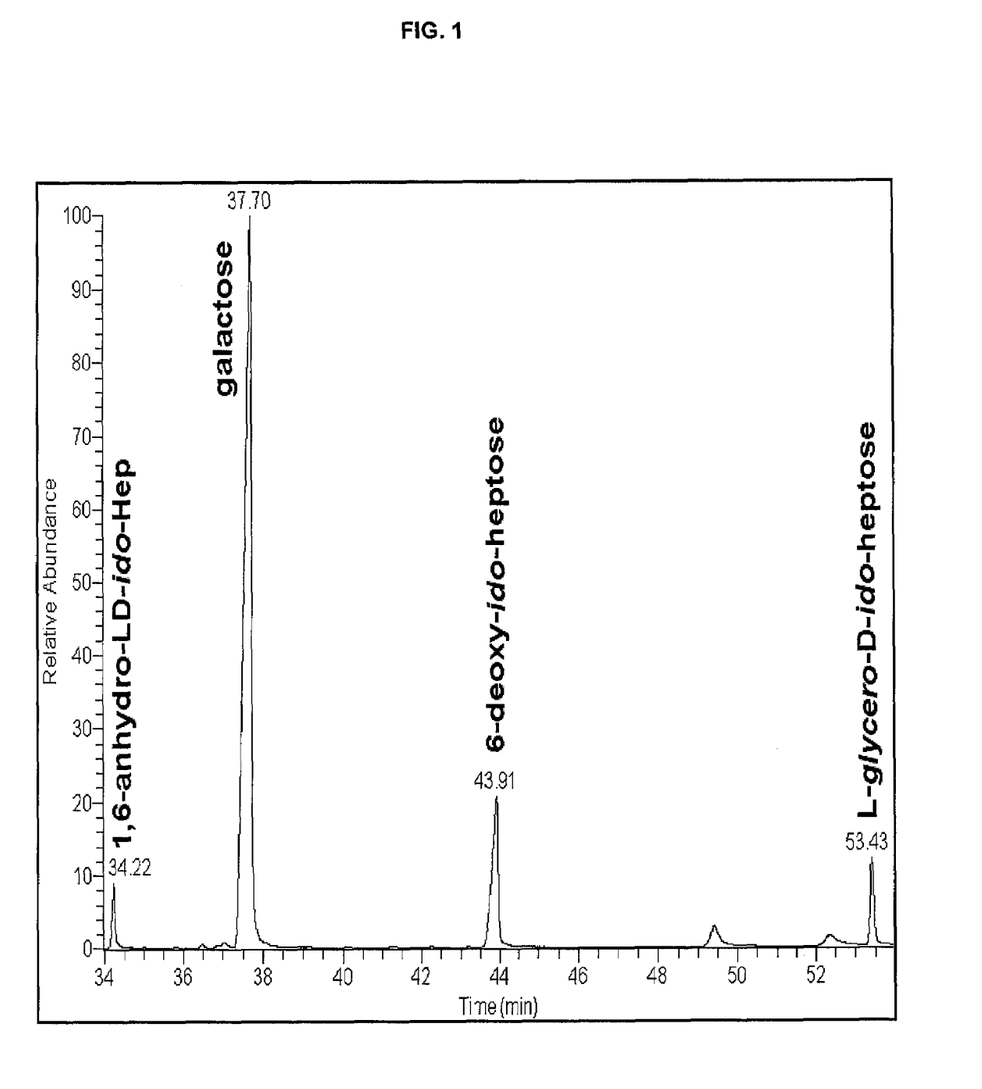
FIG. 1. Sugar composition analysis of the capsular polysaccharide of C. jejuni strain BHO 1-0142 (hereafter referred to as BHO 142) showing that this capsular polysaccharide is composed in part of D-galactose, 6-deoxy-D-ido-heptose, and L-glycero-D-ido-heptose.
Figure 2:
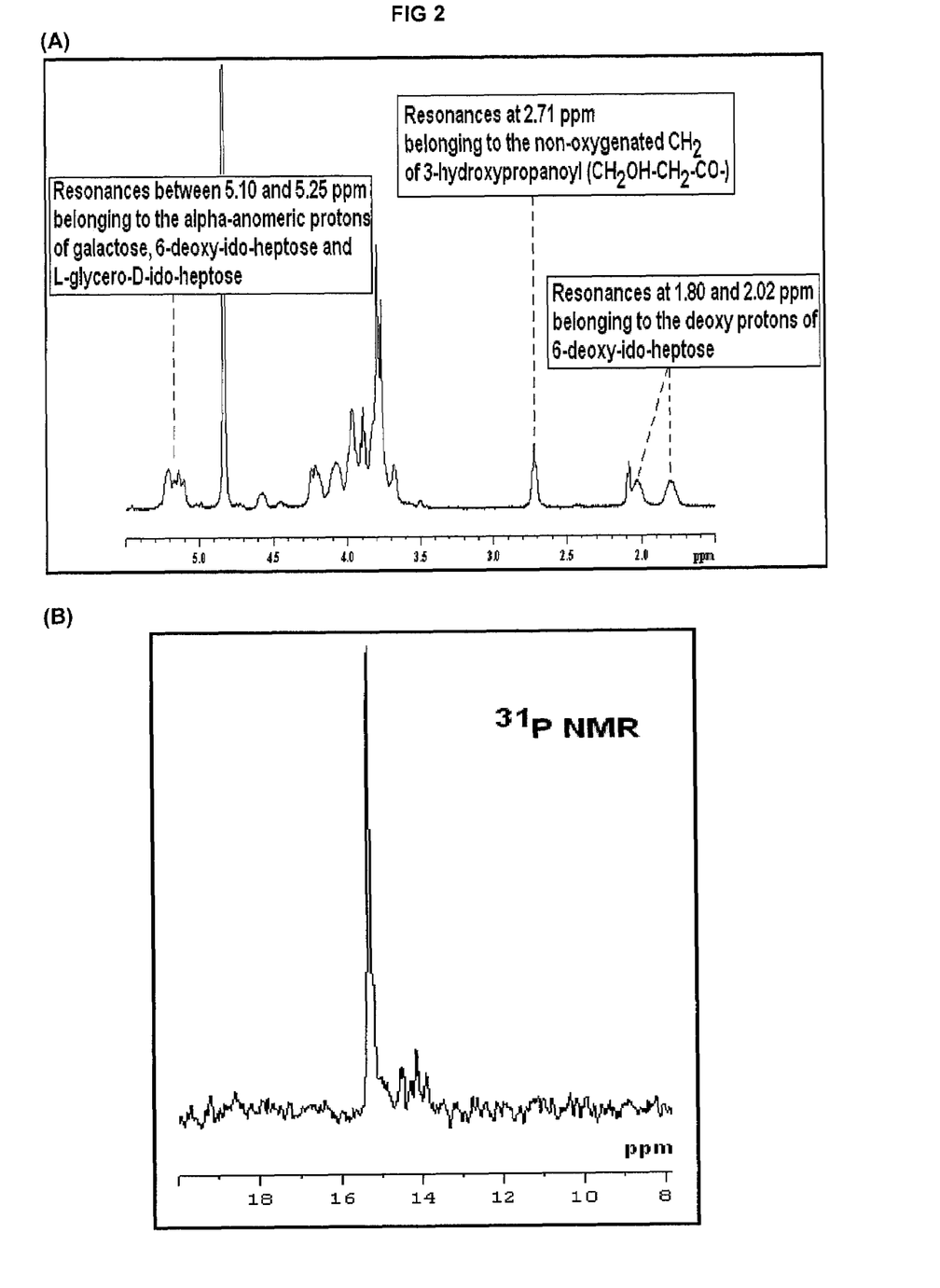
Figure 3:
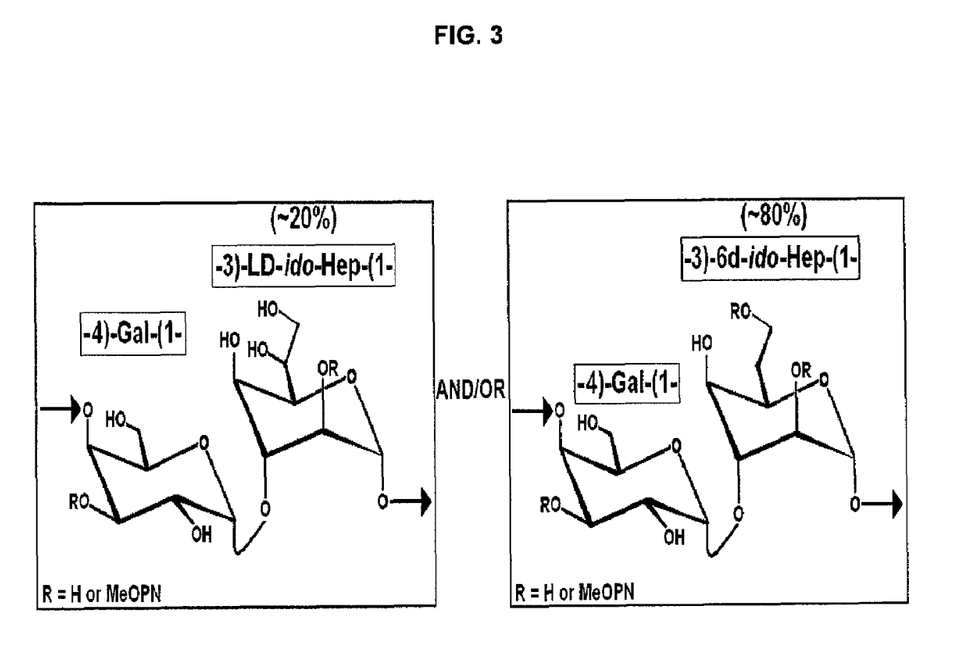
FIG. 3. The chemical structure of the disaccharide repeating blocks that make up the capsular polysaccharide of C. jejuni strain BHO 142.

Based on carbohydrate analyses as shown in FIG. 1, the capsule of *C. jejuni* strain BHO 142 (a representative of H3 serotype complex) was composed of D-galactose and 6-deoxy-D-ido-heptose, and with smaller amounts of L-glycero-D-ido-heptose. 6-anhydro-L-glycero-D-ido-heptose, a product arising from cyclization of L-glycero-D-ido-heptose during the step 1 of hydrolysis, was also observed in this analysis. Sugar linkage-type analysis showed that main monosaccharide units present were 4-substituted D-galactose and 3-substituted 6-deoxy-D-ido-heptose, and smaller amounts of 3-substituted L-glycero-D-ido-heptose also present. The 1H-NMR spectrum revealed that all units contained the alpha anomeric configuration (FIG. 2A). The $^1$H-NMR spectrum (FIG. 2A), and a 2D $^1$H-$^{13}$C HSQC experiment also yielded resonances at $\delta_H$ 2.71 and $\delta_C$ 37.20 characteristic of a non-oxygenated methylene of a 3-hydroxypropanoyl unit (7), which revealed the presence of a 3-hydroxypropanoyl ($CH_2OH$—$CH_2$—$CO$—) moiety in the capsule polysaccharide of *C. jejuni* strain BH0142. The capsular polysaccharide also contains in part O-methyl phosphoramidate units in variable concentrations (FIG. 2B). Linkage analysis data showing 3,4-disubstituted galactose, 2,3-disubstituted 6-deoxy-D-ido-heptose, 3,7-disubstituted 6-deoxy-D-ido-heptose, and 2,3-disubstituted L-glycero-D-ido-heptose, suggest that the O-methyl phosphoramidate units are present at the O-3 position of galactose, at the O-2 and/or O-7 positions of 6-deoxy-alpha-D-ido-heptose, and at the O-3 position of L-glycero-D-ido-heptose. Moreover, the linkage-type analyses show that O-methyl-phosphoramidate is mainly present at the O-3 position of galactose and at the O-2 position of 6-deoxy-alpha-D-ido-heptose. Collectively, the data showed that *C. jejuni* strain BHO 142 capsular polysaccharide (FIG. 3) was composed of a disaccharide repeating unit composed of 4-substituted alpha-D-galactose and 3-substituted 6-deoxy-alpha-D-ido-heptose. Some disaccharide repeating units (approximately 20%) contained 3-substituted L-glycero-alpha-D-ido-heptose in place of 3-substituted 6-deoxy-alpha-D-ido-heptose. Thus, the disaccharide repeating unit of the capsular polysaccharide of *C. jejuni* strain BHO 142 has the general structure (FIG. 3):

or where P represents O-methyl-phosphoramidate and is present in non-stoichiometric amounts. In some disaccharides, 3-hydroxypropanoyl may also be present.

Therefore, an aspect of this invention is an immunogenic formulation composed of isolated capsular polysaccharide composed of disaccharide repeats, each disaccharide having general formula:

where P represents O-methyl-phosphoramidate and is present in non-stoichiometric amounts. Alternatively the formulation can be composed of a capsular polysaccharide containing a mixture of both disaccharide structures. MALDI-TOF-MS analyses revealed that the average molecular weight of the BH0142 CPS analyzed here was approximately 8300 Da.

Similarly, the capsular polysaccharide of strain CG8486 was analyzed and shown to be composed of a similar structure but of a repeating disaccharide illustrate by the formula With O-methyl phosphoramidate units present in non-stoichiometric amounts at the O-2 and/or O-7 positions of 6-deoxy-beta-D-ido-Heptose. MALDI-TOF-MS analyses revealed that the molecular weight of the CG8486 CPS analyzed here was on average between 6400 and 6700 Da.

Example 1

Immunity to Capsule—can be Increase by Conjugation to Carrier Molecules

Since IgG response is often predominantly observed as a T-cell independent immune response. Therefore, children are typically only capable of mounting an IgM response in the face of polysaccharide antigens with adults capable of generating an IgG, IgA and IgM response.

In order to potentially further improve the response to capsule moieties, the immunogenicity of *C. jejuni* capsule can be conjugated to T-dependent carrier proteins.

Figure 4:
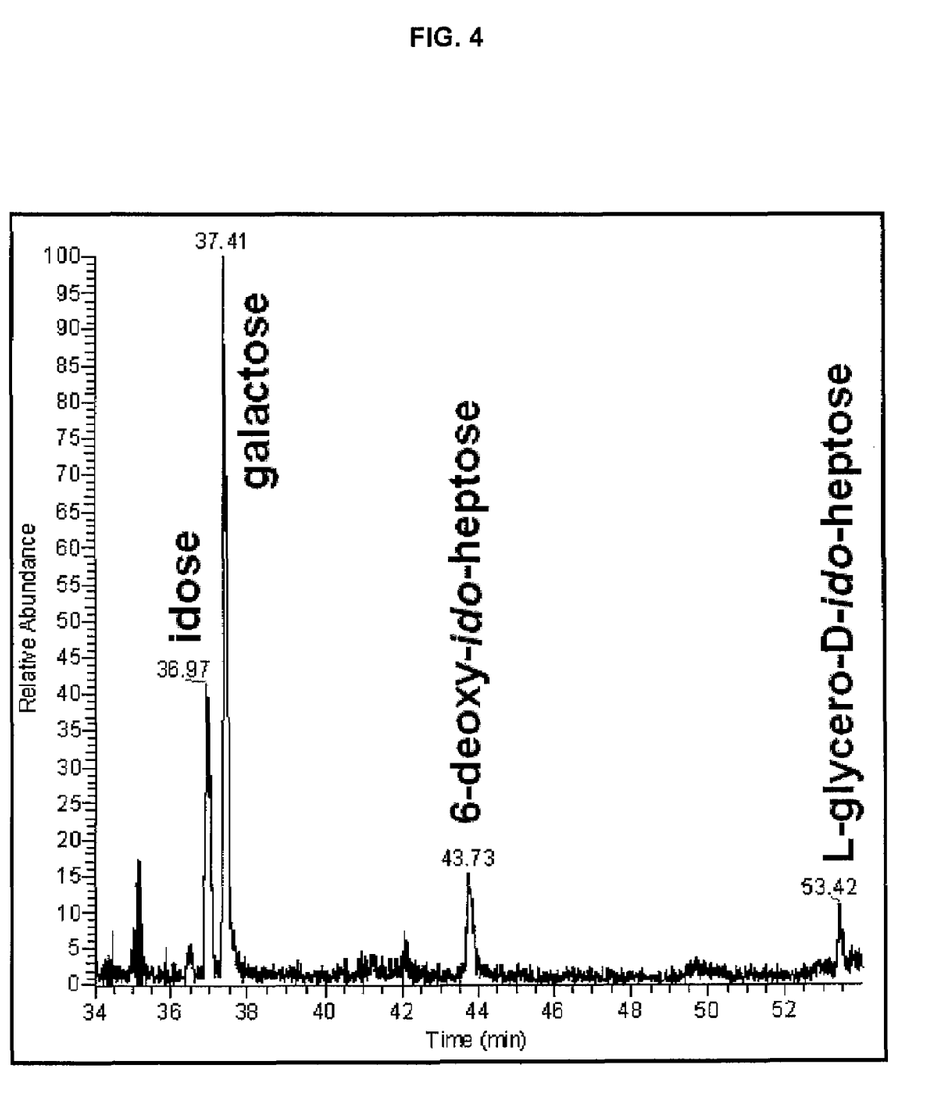
FIG. 4. Sugar composition analysis of the activated (oxidized) capsular polysaccharide of C. jejuni strain BHO 142 showing that the activated capsular polysaccharide is composed in part of idose (with an aldehyde at C-6), 6-deoxy-D-ido-heptose, and L-glycero-D-ido-heptose.

Conjugation of *C. jejuni* strain BH0142 capsular polysaccharide to a carrier protein, such as cross reacting material 197 (CRM197), can be achieved by selectively oxidizing the exocyclic glycero moiety, with periodate, of one or more L-glycero-D-ido-heptose units present in each capsular polysaccharide. Analysis (FIG. 4) of the activated (oxidized) *C. jejuni* strain BH0142 capsular polysaccharide revealed that indeed L-glycero-D-ido-heptose could be selectively oxidized to an idose unit containing an aldehyde group at C-6, with the remainder of the capsular polysaccharide intact. This activated capsular polysaccharide can be directly coupled to a carrier protein (FIG. 5A) by a reductive amination mechanism to yield a glycoconjugate composed of *C. jejuni* strain BH0142 capsular polysaccharide and a carrier protein.

Figure 5:
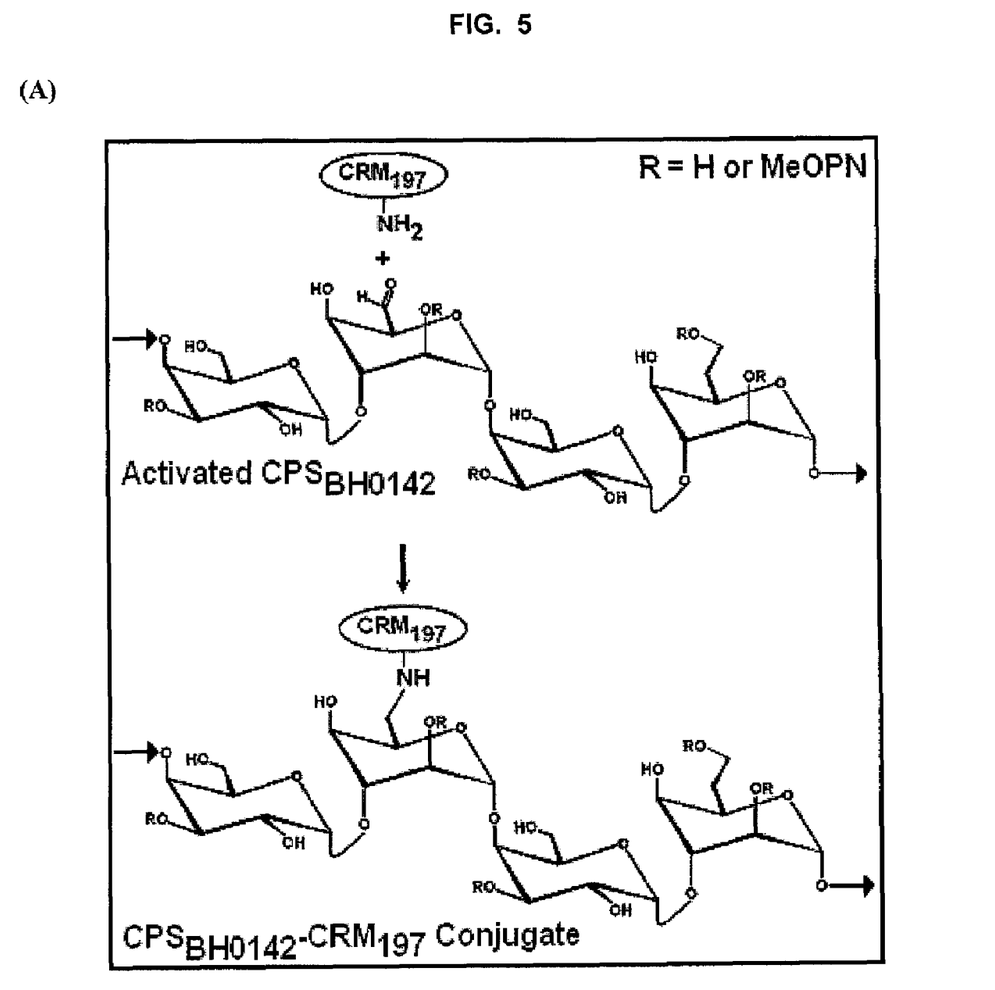

The $CPS_{8486}$-$CRM_{197}$ glycoconjugates were synthesized by covalent attachment of the CG8486 CPS to $CRM_{197}$ by reductive amination (FIG. 5B). The CG8486 CPS to $CRM_{197}$ ratio used here was 2:1 by weight. Here, the non-reducing monosaccharide of CG8486 CPS was oxidized by periodate to yield aldehyde functionalities at the non-reducing end, which served as the attachment point to $CRM_{197}$. Periodate did not oxidize the inner-regions or the reducing-end of these CPS because the lack of available vicinal hydroxyls, and the occupied reducing-ends (by the lipid anchor). Thus, only the non-reducing terminus was oxidized and the structural integrity of the CG CPS remained intact. The oxidized CG8486

CPS was analyzed by NMR, MALDI-TOF-MS and by GC-MS of the alditol acetate derivatives. The characterization of a tri-O-acetyl 1-[$^2$H$_1$]glycerol unit in the oxidized CPS was of particular interest, in that it afforded evidence that oxidation at the non-reducing end had occurred. The MALDI-TOF-MS spectra of the glycoconjugate yielded a broad m/z ions that, on average, ranged from 70000 to 80000 Da for CPS$_{8486}$-CRM$_{197}$, which implied that each CRM$_{197}$ was on average carrying up to 5 CPS$_{8486}$. It is also possible that higher molecular weight CPS$_{8486}$-CRM$_{197}$ conjugates may be present that could not be detected by MALDI-TOF-MS. Reassurance that glycoconjugates did not contain any detectable amounts of free CPS or CRM$_{197}$ was also observed in the MS spectra and/or or gel-electrophoresis, in that neither free CPS nor CRM$_{197}$ was detected in the MALDI-TOF-MS or SDS-PAGE analyses of the glycoconjugate synthesized here.

Example 2

Immunogenicity of the CG8486 Capsule Conjugate Vaccine (CPS$_{8486}$-CRM$_{197}$)

Mice were immunized with 3 doses of either 1, 5 and 25 micrograms of the capsule conjugate from CG8486 subcutaneously at four-week intervals. Blood samples were collected immediately before each vaccination and at 4, 8, 12 and 14 weeks after the third vaccination. The CPS$_{8486}$ IgG titers were determined by ELISA. Animals receiving PBS showed baseline levels of CPS$_{8486}$-specific IgG titer (geometric endpoint titer 3.4±0.40). The titers of immunized animals are shown in Table 2. Immunization with 1 µg of CG8486 capsule conjugate vaccine failed to induce CPS$_{8486}$-specific IgG. In contrast, animals immunized with 5 and 25 µg of vaccine had similar high levels of antigen-specific serum IgG after two doses. Delivery of the third dose of 5 µg of vaccine further enhanced IgG levels, but vaccination with the third dose of 25 µg of vaccine did not. The peak levels of IgG titers in the groups that received 5 µg and 25 µg of the CG8486 capsule conjugate vaccine are significantly higher than those that received either 1 µg of the vaccine or PBS, but are not significantly different than each other. After completion of the immunization series, ≧90% of the animals met the definition of responders in the groups receiving the two higher doses. CPS$_{8486}$-specific IgG levels remained elevated for at least 14 weeks after the third dose.

Example 3

Protective Efficacy of CPS$_{8486}$-CRM$_{197}$ in an Intranasal Mouse Model of C. jejuni Infection

Figure 6:
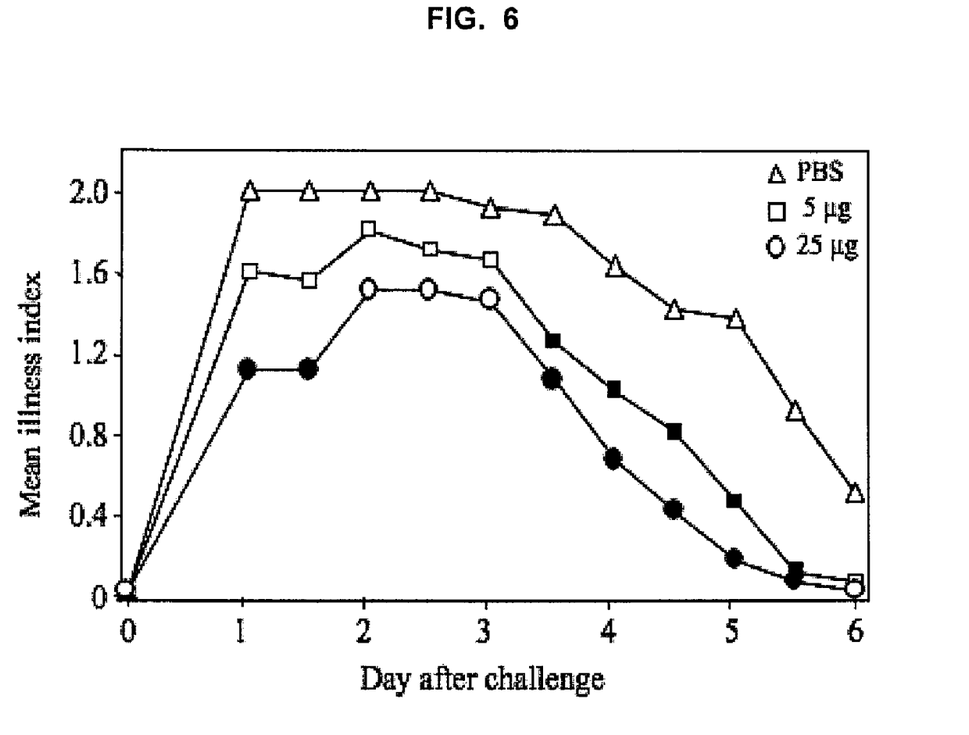
FIG. 6. Protection of mice from intra-nasal challenge with CG8486 (also referred to as CPS8486) following immunization with the CG8486 conjugate vaccine.

To determine the ability of the CG8486 capsule conjugate vaccine to protect against homologous challenge in the mouse intranasal model of infection (FIG. 6), animals immunized with 5 or 25 µg of the CG8486 capsule conjugate vaccine or PBS at 4-week intervals were challenged intranasally with C. jejuni strain CG8486. The illness indices were calculated as described in the figure legend. Vaccinated animals never reached the same level of disease severity as that seen with control animals. On days 1 and 1.5 after challenge, animals immunized with 25 µg showed significantly lower sickness than controls or the recipients of 5 µg (p<0.05), although severity of sickness increased until day 3. Three days after challenge animals immunized with either dose of the vaccine showed significantly lower sickness indices than controls (p=0.05). The mean sickness index returned to normal by day 4.5 (25 µg) or 5.5 (5 µg). In contrast, 50% of control animals remained sick for the 6-day observation period.

Example 4

Prophetic Example of Induction of Immunity to Capsule in Humans Using BH0142 Capsular Polysaccharide (CPS)

An aspect of this invention is the ability of one or more related isolated disaccharide polymers found in C. jejuni capsules to induce a vigorous and efficacious immune response in humans but not induction of contraindicating Guillain Barre Syndrome. For each vaccine formulation containing capsules from a single or mixtures of C. jejuni strains, a limited amount of experimentation is required to ascertain the optimal effective dose ranges. However, a prophetic method for the induction of anti-C. jejuni medicated diarrheal protective immunity contains the following steps:

a. priming is by administration of an immunogenic formulation containing isolated C. jejuni capsular polysaccharide composed of disaccharide repeats with the general formula

TABLE 2

Kinetics of CPS$_{8486}$-specific serum IgG after vaccination with CPS$_{8486}$-CRM$_{197}$.

| Vaccine dose (µg) | After vaccination | | | Week after vaccination 3 | | |
|---|---|---|---|---|---|---|
| | 1 | 2 | 4 | 8 | 12 | 14 |
| 1 | 3.36 ± 0.44 (0) | 3.57 ± 0.77 (10) | 3.87 ± 1.29 (20) | 3.98 ± 1.58 (20) | 3.81 ± 1.18 (20) | 3.54 ± 0.90 (10) |
| 5 | 3.42 ± 0.64 (10) | 6.42 ± 2.00 (50) | 9.85 ± 1.08 (100) | 9.65 ± 1.13 (100) | 9.23 ± 0.78 (100) | 7.55 ± 1.21 (100) |
| 25 | 3.57 ± 0.75 (10) | 8.34 ± 2.28 (80) | 10.15 ± 1.50 (100) | 9.13 ± 1.86 (90) | 9.55 ± 2.03 (90) | 8.85 ± 1.84 (100) |

*Responders were animals showing an endpoint titer of ≧1:100 (log$_e$ ≧4.6; equivalent to mean +3SD of PBS recipients). The 1 microgram doses no significant change from the base line at any time (p > 0.05); for 5 µg doses there was a significant increase after dose 2 (p < 0.001), which further increased after dose 3 (p > 0.001); for 25 µg doses there was a significant increase after dose 2 (p < 0.001), which did not increase after dose 3 (p < 0.05). For both the 5 and 25 µg doses the titers remained significantly higher post dose 1 (p < 0.001). No significant difference (p > 0.05) between IgG levels of the 5 and 25 µg doses was seen at any time.

where P represents non-stoichiometric O-methyl phosphoramidate. Alternatively the immunogenic formulation can contain a mixture of both disaccharide structures. In a preferred embodiment, the isolated disaccharides are conjugated to a carrier molecule. The immunogenic formulation can be administered orally, nasally, subcutaneously, intradermally, transdermally, transcutaneously intramuscularly, or rectally. Depending on the route of administration, the vaccine formulation can be administered with or without any of a number of adjuvants, including but not limited to LTR 192G, Aluminum hydroxide, RC529E, QS21, E294, oligodeoxynucleotides (ODN), CpG-containing oligodeoxynucleotides, aluminum phosphate, MPL® (GlaxoSmithKline, Middlesex, UK) or combinations of these or other potential adjuvants. The range of a unit dose of immunogen is 0.1 μg to 10 mg of immunogen in a range of buffer solutions.

b. Subsequent to a priming dose, 1 to 4 boosting doses can also be administered with unit dose range of 0.1 μg to 10 mg of immunogen in a buffered aqueous solution with or without adjuvant.

Example 5

Prophetic Example of Induction of Immunity to Capsule in Humans Using the $CPS_{8486}$ Capsular Polysaccharide Similar prophetic method for the induction of anti-*C. jejuni* medicated diarrheal protective immunity using $CPS_{8486}$ capsular polysaccharide contains the following steps:

(a) priming is by administration of an immunogenic formulation containing isolated *C. jejuni* capsular polysaccharide composed of disaccharide repeats with the general formula:

→3)-6-d-β-D-ido-Hep-(1→4)-β-D-GlcNAc-(1→, with O-methyl phosphoramidate units present in non-stoichiometric amounts at the O-2 and/or O-7 positions of 6-deoxy-beta-D-ido-Heptose.

In a preferred embodiment, the isolated disaccharide is conjugated to a carrier molecule. The immunogenic formulation can be administered orally, nasally, subcutaneously, intradermally, transdermally, transcutaneously intramuscularly, or rectally. Depending on the route of administration, the vaccine formulation can be administered with or without any of a number of adjuvants, including but not limited to LTR 192G, Aluminum hydroxide, RC529E, QS21, E294, oligodeoxynucleotides (ODN), CpG-containing oligodeoxynucleotides, aluminum phosphate, MPL® (GlaxoSmithKline, Middlesex, UK) or combinations of these or other potential adjuvants. The range of a unit dose of immunogen is 0.1 μg to 10 mg of immunogen in a range of buffer solutions.

(b) Subsequent to a priming dose, 1 to 4 boosting doses can also be administered with unit dose range of 0.1 μg to 10 mg of immunogen in a buffered aqueous solution with or without adjuvant.

Obviously, many modifications and variations of the present invention are possible in light of the above teachings. It is therefore to be understood that, within the scope of the appended claims, the invention may be practiced otherwise than as specifically described.

REFERENCES

1. Allos, B. M. 1997. Association between *Campylobacter* infection and Guillain Barre Syndrome. J. Infect. Dis. 176 (Suppl 2):S125-128.
2. Anderson, P. W. 1983. Antibody responses to *Haemophilus influenzae* type b and diptheria toxin induced by conjugates of oligosaccharides of the type b capsule with the non toxic protein $CRM_{197}$. Infect. Immun. 39:233-238.
3. Aspinall, G. O., S. Fujimoto, A. G. MacDonald, H. Pang, L. A. Kuryjanczyk and J. L. Penner. 1994a. Lipopolysaccharides from *Campylobacter jejuni* associated with Guillain Barre Syndrome patients mimic human gangliosides in structure. Infect. Immun. 62:2122-2125.
4. Aspinall, G. O., McDonald, A. G., and Pang, H. 1992. Structures of the O chain from lipopolysaccharides of *Campylobacter jejuni* serotypes O:23 and O:36. Carbohyr. Res. 231:13-20.
5. Aspinall, G. O., A. G. MacDonald, H. Pang, L. A. Kurjanczyk, and J. L. Penner. 1994b. Lipopolysaccharides of *Campylobacter jejuni* serotype O:19: structures of core oligosaccharide regions from the serostrain and two bacterial isolates from patients with Guillain Barre Syndrome. Biochem. 33:241-249.
6. Aspinall, G. O., A. G. MacDonald, T. S. Raju, H. Pang, L. A. Kurjanczyk, J. L. Penner and A. P. Moran. 1993. Chemical structure of the core region of *Campylobacter jejuni* serotype O:2 lipopolysaccharide. Eur. J. Biochem. 213: 1029-1037.
7. Aspinall, G. O., C. M. Lynch, H. Pang, R. T. Shaver, A. P. Moran. 1995. Chemical structures of the core region of *Campylobacter jejuni O:*3 lipopolysaccharide and an associated polysaccharide. Eur. J. Biochem. 231 (3): 570-578.
8 Baqar, S., Bourgeois, A. L., Applebee, L A., Mourad, A. S., Kleinosky, M. T., Mohran, Z., and J. R. Murphy. 1996. Murine intranasal challenge model for the study of *Campylobacter* pathogenesis and immunity. Infect. Immun. 64:4933-4939.
9. Chu, C., Schneerson, R., Robbins, J. B. and Rastogi, S. C. 1983. Further studies on the immunogenicity of *Haemophilus influenzae* type b and pneumoccocal type 6A polysaccharide-protein conjugates. Infect. Immun. 40:245-256.
10. Cover, T. L. and M. J. Blaser. 1999. The pathobiology of *Campylobacter* infections in humans. Ann. Rev. Med. 40:269-185.
11. Goon, S., J. F. Kelly, S. M. Logan, C. P. Ewing, P. Guerry. 2003. Pseudaminic acid, the major modification of *Campylobacter* flagellin, is synthesized via the Cj1293 gene. Mol. Microbiol. 50 (2):659-671.
12. Hanniffy, O. M., A. S. Shashkov, A. P. Moran, M. M. Prendergast, S. N. Senchenkova, Y. A. Knirel, and A. V. Savage. 1999. Chemical structure of a polysaccharide from *Campylobacter jejuni* 176.83 (serotype O:41) containing only furanose sugars. Carbohydr. Res. 319:124-132.
13. Jennings, H. J. Capsular polysaccharides as vaccine candidates. 1990. Curr. Top. Microbiol. Immunol. 150:97-127.
14. Jennings, H. J. and Lugowshi, C. 1981. Immunochemistry of groups A, B and C meningococcal polysaccharides-tetanus toxoid conjugates. J. Immunol. 127:1011-1018.
15. Jennings, H. J., C. W. Lugowski, F. E. Ashton, J. A. Ryan. 1983. The structure of the capsular polysaccharide obtained from a new serogroup (L) of *Neisseria meningitidis*. Carbohydr. Res. 112 (1)::105-111.
16. Karlyshev, A. V., Linton, D., Gregson, N. A., Lastovica, A. J. and Wren, B. W. 2000. Genetic and biochemical evidence of a *Campylobacter jejuni* capsular polysaccharide that accounts for Penner serotype specificity. Mol. Microbiol. 35:529-541.

17. Marburg, S., Jorn, D., Tolman, R. L., Arison, B., McCauley, J., Kniskern, P. J., Hagopian, A. and Vella, P. P. 1986. Biomolecular chemistry of macromolecules: synthesis of bacterial polysaccharide conjugates with *Neisseria meningiditis* membrane protein. J. Am. Chem. Soc. 108:5282-5287.

18. McNally, D. J., H. C. Jarrell, J. Li, N. H. Khieu, E. Vinogradov, C. M. Szymanski, and J. R. Brisson. 2005. The HS:1 serostrain of *Campylobacter jejuni* has a complex teichoic acid-like capsular polysaccharide with nonstoichiometric fructofuranose branches and O-methyl phosphoramidite groups. FEBS J. 272:4407-4422.

19. Moran, A. P., B. J. Appelmelk, and G. O. Aspinall. 1996. Molecular mimicry of host structures by lipopolysaccharides of *Campylobacter* and *Helicobacter* spp.: implications in pathogenesis. J. Endotox. Res. 3 (6):521-531.

20. Moran, A. P. and J. L. Penner. 1999. Serotyping of *Campylobacter jejuni* based on heat-stable antigens: relevance, molecular basis and implications in pathogenesis. J. Appl. Microbiol. 86:361-377.

21. Muldoon, J., A. S. Shashkov, A. P. Moran, J. A. Ferris, S, N. Senchenkova, and A. V. Savage. 2002. Structures of two polysaccharides of *Campylobacter jejuni* 81116. Carbo. Res. 337:2223-2229.

22. Parkhill, J., B. W. Wren, K. Mungall, J. M. Ketley, C. Churcher, D. Basham, T. Chillingworth, R. M. Davies, T. Feltwell, S. Holroyd, K. Jagels, A. V. Karlyshev, S. Moule, M. J. Pallen, C. W. Penn, M. A. Quail, M. A. Rajandream, K. M. Rutherford, A. H. M. van Vliet, S. Whitehead, and B. G. Barrell. 2000. The genome sequence of the food-borne pathogen *Campylobacter jejuni* reveals hypervariable tracts. Nature 403:665-668.

23. Power, P. M. and Jennings, M. P. 2003. The genetics of glycosylation in gram negative bacteria. FEMS Microbiol. Lett. 218:211-222.

24. Russell, R. G., M. J. Blaser, J. I. Sarmiento and J. Fox. 1989. Experimental *Campylobacter jejuni* infection in *Macaca nemestrina*. Infect. Immun. 57:1438-1444.

25. Russell, R. G., M. O'Donnoghue, D. C. Jr. Blake, J. Zulty and L. J. DeTolla. 1993. Early colonic damage and invasion of *Campylobacter jejuni* in experimentally challenged infant *Macaca mulatta*. J. Infect. Dis. 168:210-215.

26. Salloway, S., L. A. Mermel, M. Seamans, G. O. Aspinall, J. E. Nam Shin, L. A. Kurjanczyk, and J. L. Penner. 1996. Miller Fisher Syndrome associated with *Campylobacter jejuni* bearing lipopolysaccharide molecules that mimic human ganglioside $GD_3$. Infect. Immun. 64:2945-2949.

27. Schneerson, R., Barrera, O., Sutton, A. and Robbins, J. B. 1980. Preparation, characterization and immunogenicity of *Haemophilus influenzae* type b polysaccharide protein conjugates. J. Exp. Med. 152:361-376.

28. St. Michael, F., C. M. Szymanski, J. Li, K. H. Chan, N. H. Khieu, S. Larocque, W. W. Wakarchuk, J.-R. Brisson, and M. A. Monteiro. 2002. The structures of the lipooligosaccharide and capsule polysaccharide of *Campylobacter jejuni* genome sequenced strain NCTC 11168. Eur. J. Biochem. 269:5119-5136.

29. Szymanski, C. M., Yao, R., Ewing, C. P., Trust, T. J., and Guerry, P. 1999. Evidence for a system of general protein glycosylation in *Campylobacter jejuni*. Mol Microbiol 32:1022-1030.

30. Szymanski, C. M., Logan, S. M., Linton, D., and Wren, B. W. 2003. *Campylobacter*—a tale of two protein glycosylation systems. Trends Microbiol. 11:233-238.

31. Tauxe, R. V. 1992. Epidemiology of *Campylobacter jejuni* infections in the United States and other industrialized nations. In *Campylobacter jejuni: Current status and future trends* (Edited by Nachamkin I., Blaser M. J. and Tompkins L. S.), p. 9. American Society for Microbiology, Washington, D.C.

32. Taylor, D. N. 1992. *Campylobacter* infections in developing countries. In *Campylobacter jejuni: Current status and future trends* (Edited by Nachamkin I., Blaser M. J. and Tompkins L. S.), p. 20. American Society for Microbiology, Washington, D.C.

33. Thibault, P., Logan, S. M., Kelly, J. F., Brisson, J.-R., Ewing, C. P., Trust, T. J., and Guerry, P. 2001. Identification of the carbohydrate moieties and glycosylation motifs in *Campylobacter jejuni* flagellin. *J Biol Chem* 276: 34862-34870.

34. Young, N. M., Brisson, J.-R., Kelly, J., Watson, D. C., Tessier, L., Lanthier, P. H., Jarrell, H. C., Cadotte, N., St. Michael, F., Aberg, E., and Szymanski, C. M. 2002. Structure of the N linked glycan present on multiple glycoproteins in the gram negative bacterium, *Campylobacter jejuni*. J. Biol. Chem. 277:42530-42539.

35. Aspinall, G. O. Lipopolysaccharide and associated carbohydrate polymers from *Campylobacter jejuni* and *Helicobacter pylori*. 1998. Carbohydr. Eur. 2 1: 24-29.

36. Chen, Y-H., Poly, F, Pakulski, Z., Guerry, P., and Monteiro, M. A. 2008. The chemical structure and genetic locus of *Campylobacter jejuni* CG8486 (serotype HS:4) capsular polysaccharide: The identification of 6-deoxy-D-idoheptopyranose. Carbohydr. Res. 343: 1034-1040.

37. Baqar, S., A. L. Bourgeois, L. A. Applebee, A. S. Mourad, M. T. Kleinosky, Z. Mohran, and J. R. Murphy. 1996. Murine intranasal challenge model for the study of *Campylobacter* pathogenesis and immunity. Infect. Immun. 64:: 4933-4939.

What is claimed is:

1. An immunogenic composition, composed of an isolated carbohydrate polymer, wherein said polymer comprises a repeating disaccharide having the formula a combination thereof;
wherein P is O-methyl phosphoramidate present in non-stoichiometric amounts.

2. The immunogenic composition of claim 1, wherein said repeating disaccharide is conjugated to a carrier molecule.

3. The immunogenic composition of claim 2, wherein said carrier molecule is cross reacting material 197 ($CRM_{197}$).

4. The immunogenic composition of claim 3, wherein said carrier molecule is conjugated by reductive amination.

5. The immunogenic composition of claim 1, wherein said isolated carbohydrate polymer further comprises 3-hydroxypropanoyl.

6. A method of producing anti-*Campylobacter jejuni* immunity comprising the steps:
   a. administering the immunogenic composition of claim 1, wherein said carbohydrate polymer is conjugated or unconjugated to a carrier molecule at a dose range of 0.1 µg to 10 mg per dose with or without an adjuvant; and
   b. administering a boosting dose of said immunogenic composition with or without adjuvant at a dose range of 0.1 µg to 10 mg per dose.

7. The method of claim 6, wherein said immunogenic composition is administered with an adjuvant.

8. The method of claim 6, wherein said immunogenic composition can be administered orally, nasally, subcutaneously, intradermally, transdermally, transcutaneously intramuscularly, or rectally.

9. A method of producing anti-*Campylobacter jejuni* immunity comprising the steps:
   a. administering an immunogenic composition comprising an isolated carbohydrate polymer conjugated or unconjugated to a carrier molecule at a dose range of 0.1 μg to 10 mg per dose with or without an adjuvant; and
   b. administering a boosting dose of said immunogenic composition with or without adjuvant at a dose range of 0.1 μg to 10 mg per dose;
   wherein said isolated carbohydrate polymer comprises a repeating disaccharide having the formula

→3)-[*P*→2]-L-glycero-D-alpha-ido-Hep-(1→4)-alpha-Gal-(1→;or a combination thereof;
   where P represents O-methyl phosphoramidate present in non-stoichiometric amounts.

10. The method of claim 7, wherein said adjuvant is selected from the group consisting of LTR 192G, Aluminum hydroxide, RC529E, QS21, E294, oligodeoxynucleotides (ODN), CpG-containing oligodeoxynucleotides, aluminum phosphate.

11. The method of claim 6, wherein said carrier molecule is $CRM_{197}$.

12. An immunogenic composition, comprising an isolated *Campylobacter jejuni* capsule polysaccharide polymer, wherein said isolated polysaccharide polymer comprises a repeating disaccharide structure having the formula 13. The immunogenic composition of claim 12, wherein said isolated polysaccharide polymer is conjugated to a protein carrier molecule.

14. The immunogenic composition of claim 13, wherein said protein carrier molecule is $CRM_{197}$.

15. The immunogenic composition of claim 14, wherein said carrier molecule is conjugated by reductive amination.

16. A method of producing anti-*Campylobacter jejuni* immunity comprising the steps:
   a. administering the immunogenic composition of claim 12, with or without adjuvant at a dose range of 0.1 μg to 10 mg per dose; and
   b. administering a boosting dose of said immunogenic composition with or without adjuvant at a dose range of 0.1 μg to 10 mg per dose.

17. The method of claim 16, wherein said capsule polysaccharide is conjugated to a carrier molecule.

18. The method of claim 17, wherein said carrier is $CRM_{197}$.

19. The method of claim 16, wherein said adjuvant is selected from the group consisting of LTR 192G, Aluminum hydroxide, RC529E, QS21, E294, oligodeoxynucleotides (ODN), CpG-containing oligodeoxynucleotides, and aluminum phosphate.

20. The method of claim 16, wherein said immunogenic composition can be administered orally, nasally, subcutaneously, intradermally, transdermally, transcutaneously intramuscularly, or rectally.

21. The immunogenic composition of claim 1, wherein said isolated carbohydrate polymer contains 2-100 said disaccharide.

22. The immunogenic composition of claim 9, wherein said isolated carbohydrate polymer contains 2-100 said disaccharide.

23. The immunogenic composition of claim 12, wherein said isolated polysaccharide polymer contains 2-100 said disaccharide.

24. The immunogenic composition of claim 16, wherein said isolated polysaccharide polymer contains 2-100 said disaccharide.

25. The immunogenic composition of claim 12, wherein said disaccharide further comprises O-methyl phosphoramidate at O-2 or O-7 positions of 6-deoxy-beta-D-ido-Heptose.

26. The immunogenic composition of claim 16, wherein said disaccharide further comprises O-methyl phosphoramidate at O-2 or O-7 positions of 6-deoxy-beta-D-ido-Heptose.

* * * * *